United States Patent [19]

Neuder

[11] Patent Number: 4,968,229
[45] Date of Patent: Nov. 6, 1990

[54] PRESSURE INFUSION APPARATUS

[75] Inventor: Klaus Neuder, Obertshausen, Fed. Rep. of Germany

[73] Assignee: Fresenius AG, Bad Homburg, Fed. Rep. of Germany

[21] Appl. No.: 393,978

[22] Filed: Aug. 15, 1989

[30] Foreign Application Priority Data

Aug. 16, 1988 [DE] Fed. Rep. of Germany ....... 3827722

[51] Int. Cl.$^5$ .............................................. F04B 43/12
[52] U.S. Cl. ...................................... 417/474; 417/477
[58] Field of Search ............... 417/360, 361, 474, 475, 417/476, 477; 604/153; 128/DIG. 12

[56] References Cited

U.S. PATENT DOCUMENTS

| | | | |
|---|---|---|---|
| 4,025,241 | 5/1977 | Clemens | 417/477 |
| 4,138,205 | 2/1979 | Wallach | 417/360 |
| 4,184,815 | 1/1980 | Casson et al. | 417/477 |
| 4,191,184 | 3/1980 | Carlisle | 604/153 |
| 4,218,197 | 8/1980 | Meyer et al. | 417/477 X |
| 4,256,442 | 3/1981 | Lamadrid et al. | 417/477 |
| 4,472,116 | 9/1984 | Wenstrup | 417/477 |
| 4,472,117 | 9/1984 | Wenstrup | 417/477 |
| 4,552,516 | 11/1985 | Stanley | 417/477 |
| 4,558,996 | 12/1985 | Becker | 417/477 X |
| 4,813,855 | 3/1989 | Leveen et al. | 417/477 |
| 4,824,339 | 4/1989 | Bainbridge et al. | 417/477 |
| 4,861,242 | 8/1989 | Finsterwald | 417/477 |

Primary Examiner—Leonard E. Smith
Assistant Examiner—Eugene L. Szczecina, Jr.
Attorney, Agent, or Firm—Marshall, O'Toole, Gerstein, Murray & Bicknell

[57] ABSTRACT

To enable geriatric or morbid users to be able to insert a delivery tube (11) into a pressure infusion apparatus (1) between the delivery or pumping mechanism (3, 23) and pressure or application means (2, 22, 32) a cam plate is arranged which bears with a portion of its outer periphery on the pressure means which presses against the action of a spring against the cam plate. Via rotation direction-dependent drivers (8) the cam plate is connected to the delivery mechanism (3, 23) in such a manner that for a given direction of rotation the delivery mechanism (3, 23) and the pressure means can be moved towards or away from each other.

6 Claims, 4 Drawing Sheets

PRESSURE INFUSION APPARATUS

BACKGROUND OF THE INVENTION

The invention relates to a pressure infusion apparatus comprising a drive which exerts a periodic pressure movement via a delivery mechanism (such as rotor or finger peristalsis) advancing during delivery on a section of a flexible tube in which the medium to be delivered is disposed, and a pressure means stationary during the delivery, such as pressure plate, stator or tube plate.

Pressure infusion apparatuses are used for pumping infusion fluids or solutions which are disposed in a supply vessel into the vein of a patient at a rate desired in accordance with the particular therapy. The pressure infusion apparatus is disposed at a connecting tube between the supply vessel and a cannula. Pressure infusion apparatuses of various constructions are known.

One known construction comprises a stator and a rotor driven by a motor, with a flexible pump tube or hose being clamped between the rotor and stator. By the rotation of the rotor the hose or tube is continuously compressed in the direction toward the patient, and the infusion solution disposed in the tube is thereby being pumped at a predetermined rate into the vein.

Such a pressure infusion apparatus is known, for example, from Carson, et al. U.S. Pat. No. 4,184,815 (Jan. 22, 1980). To insert the tube the rotor must be turned by hand into a predetermined position in order to prevent squeeze rollers arranged on the rotor from obstructing insertion. After a portion of the tube has been placed between the rotor and stator the rotor must be further turned by hand, with the first squeezer roller then already pressing against the tube. For this purpose the user (physician, nurse, patient, etc.) must exert a specific force.

In a peristaltic pump as is known from Clemens U.S. Pat. No. 4,025,241 (May 24, 1977), for example, the stator must be pressed away from the rotor against the force of two springs for the tube segment to be inserted.

Peristaltic pumps may be equipped with a finger peristalsis mechanism in which a large number of fingers or pump rams are arranged in a straight line adjacent each other. The infusion tube filled with the medium to be delivered is clamped between the free ends of the pump rams and a pressure plate. The solution in the infusion tube is delivered by a peristaltic movement of the pump rams. With this construction as well the user must press a pressure plate away from the pump rams against the action of a spring in order to insert the infusion tube.

Finally, statorless roller pumps are also known in which the tube is secured in a tube plate in such a manner that the tube segment forms a loop. For inserting the tube segment the loop must be placed over the rotor and the tube plate inserted into a holder. Loop size and rotor/holder spacing are adapted to each other in such a manner that on insertion of the tube plate into the holder the tube is compressed by the rollers of the rotor. This pretensioning of the tube segment also requires the application of a certain force on the part of the user.

In all known prior pressure infusion apparatuses the application or pressure means for the tube must be lifted off the delivery mechanism or applied by mechanical work on the part of the user. This is done either by direct gripping of the application or pressure means or delivery mechanism or by indirect "gripping" with the aid of levers or knobs.

It is also known to intermediately store part of the mechanical work applied by the user on opening or closing the pressure application means in order then to enable closure or opening of the pressure means by the application of less force. In each case however it is the user who must do the mechanical work.

SUMMARY OF THE INVENTION

One problem addressed by the invention is to improve a pressure infusion apparatus in such a manner that the necessary work for opening or closing the pressure means is not applied by the user but by an opening mechanism disposed inside or outside the apparatus so that the pressure infusion apparatus can also be employed by a geriatric and/or morbid user.

This problem is solved by disposing a cam plate between the delivery mechanism and a pressure means with a portion of the outer periphery of the cam plate bearing on the pressure means, which under the action of a force presses against the cam plate and which via rotation direction-dependent drivers is connected to the delivery mechanism so that with a predetermined direction of rotation the delivery mechanism and the pressure means are movable toward or away from each other.

To convey or deliver the infusion solution in the pressure infusion apparatus a drive is employed which is usually required only in one direction of rotation. The other direction of rotation is free and according to the invention is used for actuating the opening mechanism. By using the drive already present the user only needs to press a button to actuate the opening and closing operation, thus requiring only a fraction of the work which is required for direct opening and closing of the application or pressure means. The reduced amount of work required for opening and closing provides better handling by geriatric and/or morbid users.

Other objects and advantages of the invention will be apparent to those skilled in the art from a review of the following detailed description taken in conjunction with the drawings and the appended claims.

DETAILED DESCRIPTION OF PREFERRED EMBODIMENTS OF THE INVENTION

Figure 1:
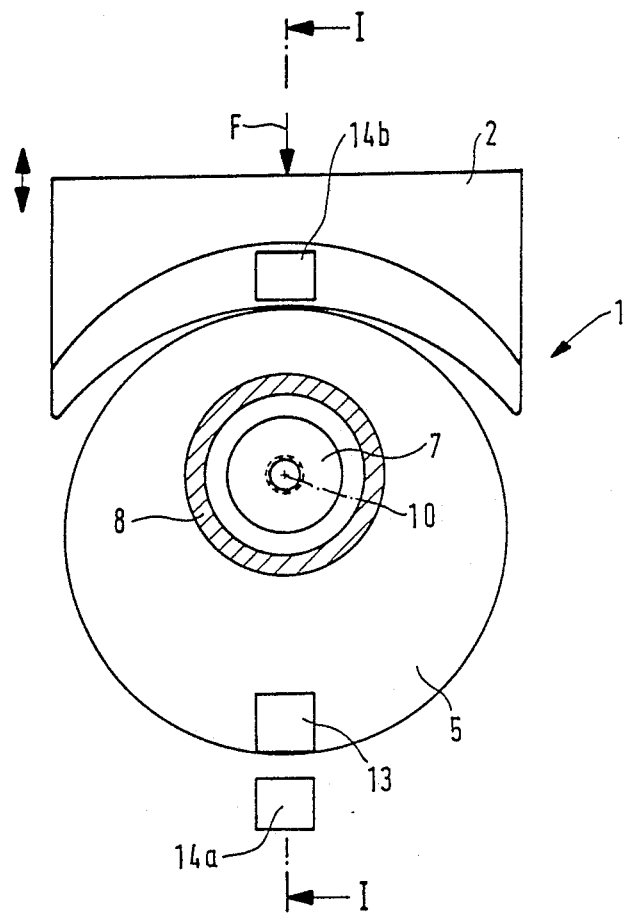
FIG. 1 is a plan view of one embodiment of a cam plate and stator of the invention.

The function of the inventive pressure infusion apparatus is based on the fact that a cam plate can press pressure means for an infusion tube away from or against a delivery or pumping mechanism depending on the rotational angle of the delivery mechanism. The force-locking contact between the pressure means and the cam plate is ensured by a force which is directed against the pressure means and which can be applied, for example, by a spring. By at least one rotation direction-dependent entrainer or driver the cam plate can then be coupled to the delivery means when the delivery means moves oppositely to the delivery direction.

The necessary energy for opening the pressure means is applied here by the motor drive unit of the pump. By known electronic or mechanical steps it is possible to ensure that the user can open the stator only when the pump is not switched to delivery.

According to a particular embodiment the cam plate is circular and its center of rotation is eccentrically disposed. In a pressure infusion apparatus comprising a rotor and stator the cam plate is disposed beneath the rotor, with the center of rotation of the cam plate and the center of rotation of the rotor coinciding.

To enable the "opening" and "closing" to be automated a position detection of the cam plate is necessary. This is achieved according to one embodiment by disposing in or on the cam plate a magnet which cooperates with at least one Hall sensor which is mounted, for example, on the housing at a predetermined angular position of the cam plate. Preferably, two Hall sensors are arranged at the 0° and 180° positions of the cam plate and mark the open position and the closed position. The direction of rotation leading to opening and closing of the pressure means is opposite to the direction of rotation employed for delivering the infusion solution.

Various components may be employed as drivers.

Thus, the drivers may comprise at least one tooth pawl which is mounted at one end on the cam plate or the delivery mechanism. When the direction of rotation of the delivery mechanism is changed, i.e. from "delivery" to "opening", the pawl engages at its other end into a corresponding recess in the delivery mechanism or in the cam plate.

According to another embodiment the drivers comprise two textile strips which bear on each other with their respective piles. The pile alignment of the two textile strips is in opposite directions so that the two piles interengage only in one direction of movement and thus establish a force-locking connection between delivery mechanism and pressure means.

According to a further embodiment the drivers comprise at least one spiral spring which with one end secured to the cam plate or the delivery mechanism, and for a given direction of rotation the other end engaging a corresponding recess in the delivery mechanism or in the cam plate.

The drive of the pressure infusion apparatus is controlled and constructed in such a manner that the opening and closure takes place automatically.

Figure 2:
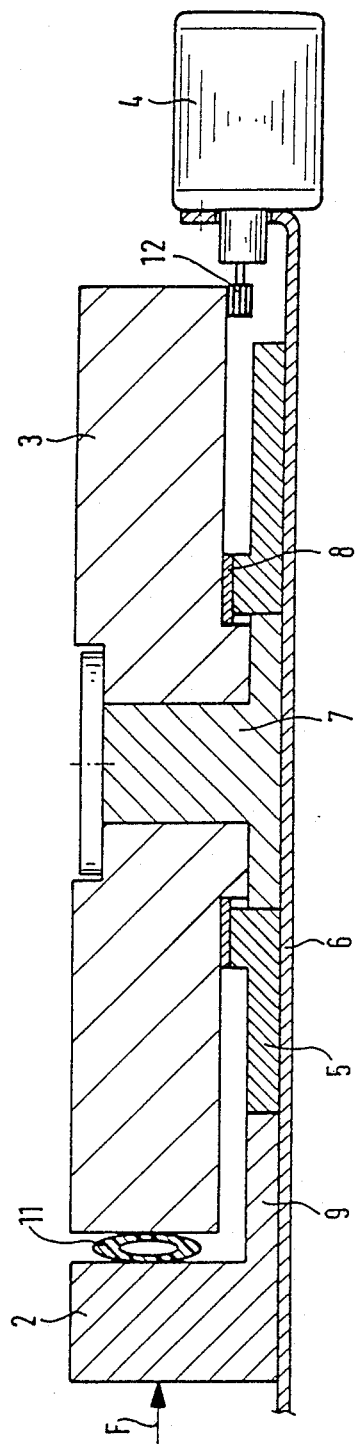
FIG. 2 is a section taken along line I—I of the embodiment of FIG. 1.

In FIGS. 1 and 2 a pressure infusion apparatus generally designated 1 with a rotor 3 (see FIG. 2) and stator 2 is schematically illustrated. A cam plate or disc 5 has an eccentrically arranged rotation center designated 10 which coincides with the rotation center of the rotor 3. The cam plate 5 is rotatably mounted by means of a bearing block 7. At the upper side of the cam plate a rotation direction-dependent driver or dog 8 is schematically indicated which hereinafter will be described in more detail with reference to FIGS. 5a, 5b and 5c. The cam plate 5 bears with a portion of its outer periphery on the stator 2 which is pressed with a force F against the cam plate 5. This force F can be applied by a spring which is not shown.

The cam plate 5 is provided with a magnetic region 13 which for position detection of the cam plate 5 cooperates with two Hall sensors 14a and 14b. The position of the cam plate shown in FIG. 1 is the closure position. If the cam plate is turned through 180° the open position is reached and is then registered by the sensor 14b which switches off the drive. If after insertion of a tube 11 (see FIG. 2) the stator is to be brought into the closure position, with the same direction of rotation as before the cam plate 5 is again moved on through 180° until the magnet 13 lies opposite the sensor 14a which then switches a drive 4 (FIG. 2) to "deliver", i.e. in the opposite direction of rotation. With the opposite direction of rotation the rotor 3 and cam plate 5, due to the form of the drivers 8, come out of engagement so that during delivery the cam plate 5 is at rest.

As best seen in FIG. 2, the stator 2 is displaceably arranged with respect to the rotor 3 or the cam plate 5 on a common base plate 6. The stator 2 comprises an extension 9 which projects beneath the rotor 3 and bears on the cam plate 5. Between the stator 2 and rotor 3 a squeezed tube 11 is shown in a closure position. The rotor 3 and the cam plate 5 are arranged rotatably by means of the bearing block 7. The rotor 3 is driven via a gear 12 by a drive 4 which also comprises a gear. At the upper side of the cam plate 5 a rotation direction-dependent drive 8 is disposed which in accordance with a predetermined direction of rotation of the rotor 3 sets the cam plate 5 in the direction of rotation so that the stator 2 is opened or closed.

Figure 3:
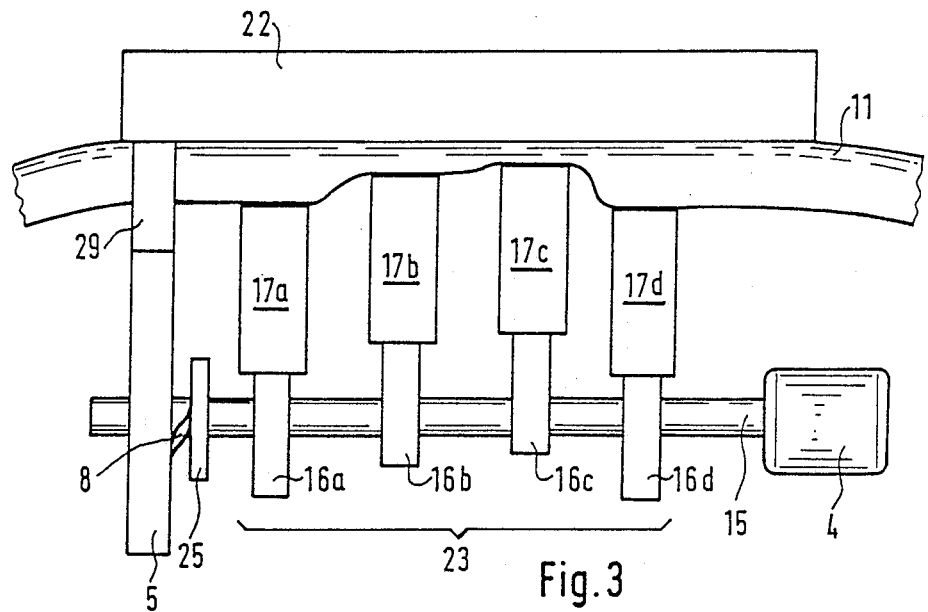
FIG. 3 shows a further embodiment of the invention in a peristaltic pump.

FIG. 3 schematically illustrates a pressure infusion apparatus with a finger peristalsis apparatus. A pumping or delivery mechanism generally designated 23 comprises in the illustrated embodiment four pump rams 17a–d which are connected via corresponding cam plates 16a–d to a drive shaft 15. Due to the arrangement and shape of the cam plates 16a–d the pump rams 17a–d execute a peristaltic motion by which solution in the tube 11 is conveyed. The application or pressure means lying opposite the pump rams 17a–d in the illustrated embodiment is a pressure plate 22 having an extension 29 which bears on a portion of the outer periphery of the cam plate 5. As in the embodiments of FIGS. 1 and 2 the cam plate 5 may be circular, with the center of rotation being disposed eccentrically. The cam plate 5 is rotatably mounted on the drive shaft 15 and is operatively connected to the delivery mechanism 23 via a driver 8 and a further plate 25 fixedly secured to the drive shaft 15.

When the drive shaft 15 moves in the delivery direction, i.e. the pump rams 17a–d execute a peristaltic motion, the cam plate 5 is not in engagement with the mechanism 23. When, however, the direction of rotation of the drive shaft 15 is reversed the driver 8, in this case constructed as tooth pawl, engages a corresponding recess in the cam plate 5 and rotates the latter in the direction of rotation of the shaft 15. As a result the pressure plate 22 is moved away from the delivery mechanism 23 so that the tube 11 is freed and can be removed from the pressure infusion apparatus. After replacement of the tube 11 the drive shaft 15 is further rotated in the same direction and as a result the cam plate 5 also further rotates in the same direction. The pressure disc 22 is thereby again brought into the closure position.

Figure 4:
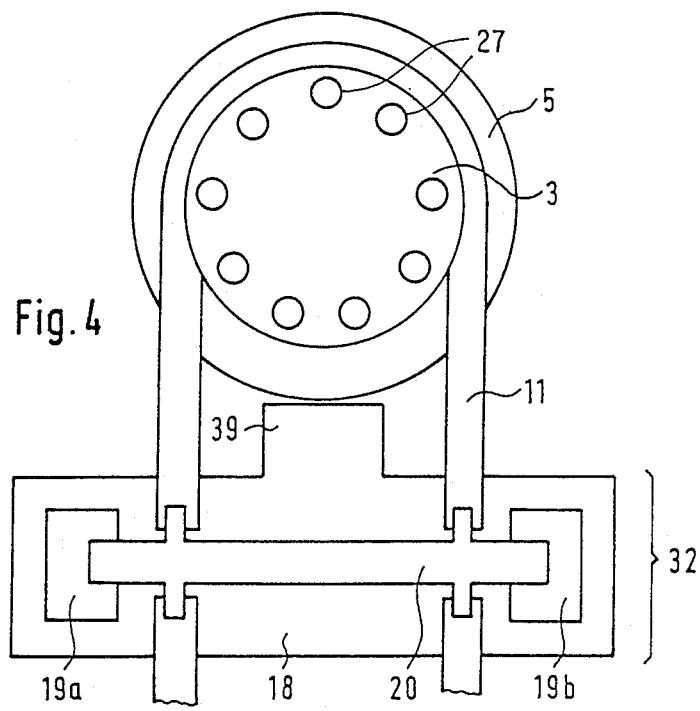
FIG. 4 shows a further embodiment of the invention in a statorless pump.

FIG. 4 schematically illustrates a statorless pump comprising a rotor 3 having a number of rollers 27 arranged circularly. A tube 11 is curved to form a loop and secured to a tube plate 20. Beneath the rotor 3 in a manner similar to the embodiment of FIG. 2 the cam plate 5 is disposed and bears with a portion of its outer periphery on an extension 39 of a pressure plate 18. Two holders 19a and 19b are secured on the upper side of the pressure plate 18. The tube plate 20 is inserted into the holders 19a and 19b.

For insertion of the tube 11 the pressure means 32 is moved by means of the cam plate 5 toward the rotor 3. The tube segment 11 can then be placed over the rotor and the tube plate 20 can be inserted without applying additional force into the holders 19a and 19b. Thereafter the cam plate 5 is further rotated and as a result the pressure means 32 is moved away from the rotor 3. The tube 11 is thereby tensioned and the rollers 27 compress the tube in the upper portion to such an extent that on rotation of the rotor 3 in the delivery direction the solution disposed in the tube 11 is conveyed. In such pumps, in contrast to the pressure infusion apparatuses of the prior art, the open position is achieved by a moving together of the rotor and pressure means and the closure position by a moving apart thereof.

Figure 5A:
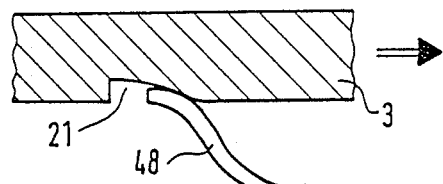
FIGS. 5a, 5b, and 5c show three embodiments of drivers of the invention.
Figure 5B:
Figure 5C:
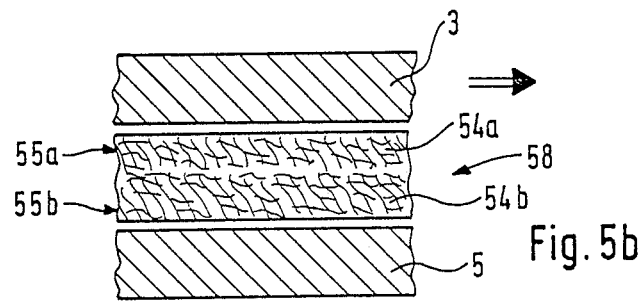

In FIGS. 5a, 5b, and 5c three embodiments of the drivers 8 are shown. In FIG. 5a the driver 8 comprises a tooth pawl 48 which is secured with one end on the cam disc 5. With its other end the driver 48 engages a recess 21 in the rotor 3 when the rotor 3 moves in the direction of the arrow. In this case the cam plate 5 is constrained in this direction. When the rotor 3 moves oppositely to the direction of the arrow the pawl 48 comes out of engagement with the rotor 3 so that the cam plate 5 is not constrained.

In FIG. 5b the drivers 58 comprise two textile strips 55a and 55b comprising piles denoted by the reference numerals 54a and 54b, respectively. The piles 54a and 54b are aligned in opposite directions so that on a movement of the rotor 3 in the direction of the arrow the cam plate 5 is constrained.

In FIG. 5c the driver 8 comprises a spiral spring 68 which is secured with one end to a pin 3' of the rotor 3. With the other end the spiral spring engages a corresponding recess 21 of the cam plate 5. The mode of operation corresponds to the embodiment illustrated in FIG. 5a.

The foregoing detailed description is given for clearness of understanding only, and no unnecessary limitations should be understood therefrom, as modifications within the scope of the invention will be apparent to those skilled in the art.

I claim:

1. Pressure infusion apparatus comprising a drive which exerts, via a delivery mechanism, an advancing periodic pressure movement during delivery on a section of a flexible tube containing a medium to be delivered, and a pressure means which is stationary during delivery, characterized in that a cam plate (5) is disposed between the delivery mechanism (3, 23) and the pressure means (2, 22, 32), a portion of the outer periphery of said cam plate (5) bearing on the pressure means (2, 22, 32) which under the action of a force presses against the cam plate (5) and which is connected to the delivery mechanism (3, 23) by means of a rotation direction-dependent driver (5, 58, 68) such that with a predetermined direction of rotation the delivery mechanism (3, 23) and the pressure means (2, 22, 32) are selectively movable toward or away from each other.

2. Pressure infusion apparatus according to claim 1, characterized in that the cam plate (5) is circular and comprises an eccentrically disposed rotation center (10).

3. Pressure infusion apparatus according to claim 1 characterized in that the cam plate (5) comprises a magnetic region (13) which cooperates with at least one Hall sensor (14a, 14b) for position detection.

4. Pressure infusion apparatus according to claim 1 characterized in that the driver comprises at least one pawl (48) which is secured at a first end thereof to the cam plate (5) or the delivery mechanism (3, 23) and for a given direction of rotation engages at a second end thereof a corresponding recess (21) in the delivery mechanism (3, 23) or in the cam plate (5).

5. Pressure infusion apparatus according to claim 1 characterized in that the driver comprises textile strips (55a, 55b) each having oppositely aligned pile (54a, 54b), one textile strip (55a or 55b) being secured to the cam plate (5) and one textile strip (55b or 55a) being secured to the delivery mechanism (3, 23).

6. Pressure infusion apparatus according to claim 1 characterized in that the driver comprises at least one spiral spring (68) which is secured at a first end thereof to the cam plate (5) or the delivery mechanism (3, 23) and for a given direction of rotation engages at a second end into a corresponding recess (21) in the delivery mechanism (3, 23) or in the cam plate (5).

* * * * *